United States Patent [19]

Culbert

[11] Patent Number: Plant 5,521

[45] Date of Patent: Jul. 23, 1985

[54] CHRYSANTHEMUM PLANT NAMED ILLINI HARVEST

[75] Inventor: John R. Culbert, Clinton, Ill.

[73] Assignee: University of Illinois, Chicago, Ill.

[21] Appl. No.: 488,071

[22] Filed: Apr. 25, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of chrysanthemum named Illini Harvest characterized by its flat capitulum form and single anemone capitulum type; red bronze ray florets and yellow-green to golden yellow cushion of disc florets; 55–65 mm. diameter across face of capitulum; excellent flower production, and by its medium pot plant height and semi-upright branching pattern.

2 Drawing Figures

The present invention comprises a new and distinct cultivar of *Chrysanthemum morifolium,* Ramat., named Illini Harvest.

Illini Harvest is a product of a planned breeding program which had the objectives of creating new chrysanthemum cultivars with single anemone capitulum type, red bronze ray floret color, 9 week response, and with the ability to produce commercially acceptable quality in year round pot mum programs. Such traits in combination were not present in previously available commercial cultivars.

Illini Harvest was originated from a hybridization made in a controlled breeding program in Urbana, Ill. in 1976. The female parent was identified as 18-01-74 and the male parent as 6-06-73. Illini Harvest was discovered and selected as one flowering plant within the progeny of the selected parentage by John R. Culbert in July, 1977 in a controlled environment at Urbana, Ill., and subsequently given the code name FP-Ill-76-127.

The first act of asexual reproduction of Illini Harvest was accomplished when vegetative cuttings were taken from the initial selection in September, 1977 in a controlled environment in Urbana, Ill. by a technician working under formulations established and supervised by John R. Culbert. Horticultural examination of selected units initiated Dec. 28, 1977 has demonstrated that the combination of characteristics as herein disclosed for Illini Harvest are firmly fixed and are retained through successive generations of asexual reproduction.

Illini Harvest has not been observed under all possible environmental conditions. The phenotype may vary significantly with variations in environment such as temperature, light intensity, and day length. The following observations, measurements and comparisons describe plants grown in Urbana and West Chicago, Ill. and Parrish, Fla. under greenhouse conditions which approximate those generally used in commercial practice.

The following traits have been repeatedly observed and are determined to be basic characteristics of Illini Harvest, which in combination distinguish this chrysanthemum as a new and distinct cultivar:

1. Flat capitulum form.
2. Single anemone capitulum type.
3. The anemone disc florets are more developed and pronounced under certain conditions. Under high temperatures they are smaller and less pronounced than under low temperatures.

4. Red bronze ray florets, providing good contrast with flat cushion of disc florets; good color retention.
5. Diameter across the face of the capitulum is 55–65 mm.
6. Medium pot plant height, about 280 mm. from edge of the pot.
7. Semi-upright branching pattern.
8. Yellow-green (immature) to golden yellow (mature) disc florets.
9. Excellent flower production.

Of the many commercial cultivars known to the present inventor, the most similar in comparison to Illini Harvest is Illini Sunset, the characteristics of which are disclosed in my pending application. Reference is made to attached Chart A which compares certain characteristics of Illini Harvest to those same characteristics of Illini Sunset. Generally, Illini Harvest is distinguished from the comparison cultivar by its red bronze ray florets, larger diameter across disc florets, consistent anemone type, taller plant height, and its somewhat later response.

The accompanying photographic drawings show typical inflorescence and foliage characteristics of Illini Harvest, with colors being as nearly true as possible with illustrations of this type. Sheet 1 is a color photograph of Illini Harvest, and sheet 2 is a black and white print of the underside typical foliage of Illini Harvest at various stages of growth.

In the following description color references are made to The Royal Horticultural Society Color Chart. The color values were determined between 8:00–9:00 A.M. on Apr. 25, 1983 under 2000–3000 foot candles at Parrish, Fla.

Classification:

*Botanical.*—*Chrysanthemum morifolium,* Ramat., CV ILLINI HARVEST.

*Commercial.*—Pot Mum.

INFLORESCENCE

A. Capitulum:

*Form.*—Flat; ray florets are rather narrow and long, approximately 30 ray florets in 1–2 rows; flat cushions of disc florets blend nicely with ray florets.

*Type.*—Single anemone.

*Diameter across face.*—55–65 mm.

*Number.*—18–20 Flowers per plant, with expanded range depending on season and culture.

B. Corolla of ray florets:

*Color (general tonality from a distance of three meters).*—Red.

*Color (upper side).*—46A Fading to 178D.

*Color (underside).*—179D.

C. Corolla of disc florets:

*Color (mature).*—Golden yellow.

*Color (immature).*—Lime-green.

D. Reproductive organs:

*Androecium.*—Present disc florets only — many.

*Gynoecium.*—Present both ray and disc florets — many.

PLANT

A. General appearance: Slightly spreading but generally upright, with abundant foliage; medium plant height, 280 mm.

B. Foliage:

*Color (abaxial).*—147B.

*Color (adaxial).*—147A.

CHART A

COMPARISON OF ILLINI HARVEST AND ILLINI SUNSET

| CULTIVAR | RAY FLORET COLOR | CAPITULUM TYPE & FORM | DIAMETER ACROSS FACE OF CAPITULUM |
|---|---|---|---|
| ILLINI HARVEST | Dark Bronze | Flat daisy or semi-anemone type when grown cool | 50–65 mm. |
| ILLINI SUNSET | Maroon-Pink | Flat daisy anemone type when grown cool | 55–65 mm. |

| CULTIVAR | PLANT HEIGHT | FLOWERING RESPONSE PERIOD | DIAMETER ACROSS DISC. ANEMONE FORM |
|---|---|---|---|
| ILLINI HARVEST | 280 mm. | 9 weeks | 22–26 mm. |
| ILLINI SUNSET | 250 mm. | 8 weeks | 15–18 mm. |

Comparison made of plants grown as 6" pot plants in Parrish, Florida

I claim:

1. A new and distinct cultivar of chrysanthemum named Illini Harvest, as illustrated and described, and particularly characterized by its flat capitulum form and single anemone capitulum type; red bronze ray florets and yellow-green to golden yellow cushion of disc florets; 55–65 mm. diameter across face of capitulum; excellent flower production, and by its medium pot plant height and semi-upright branching pattern.

* * * * *

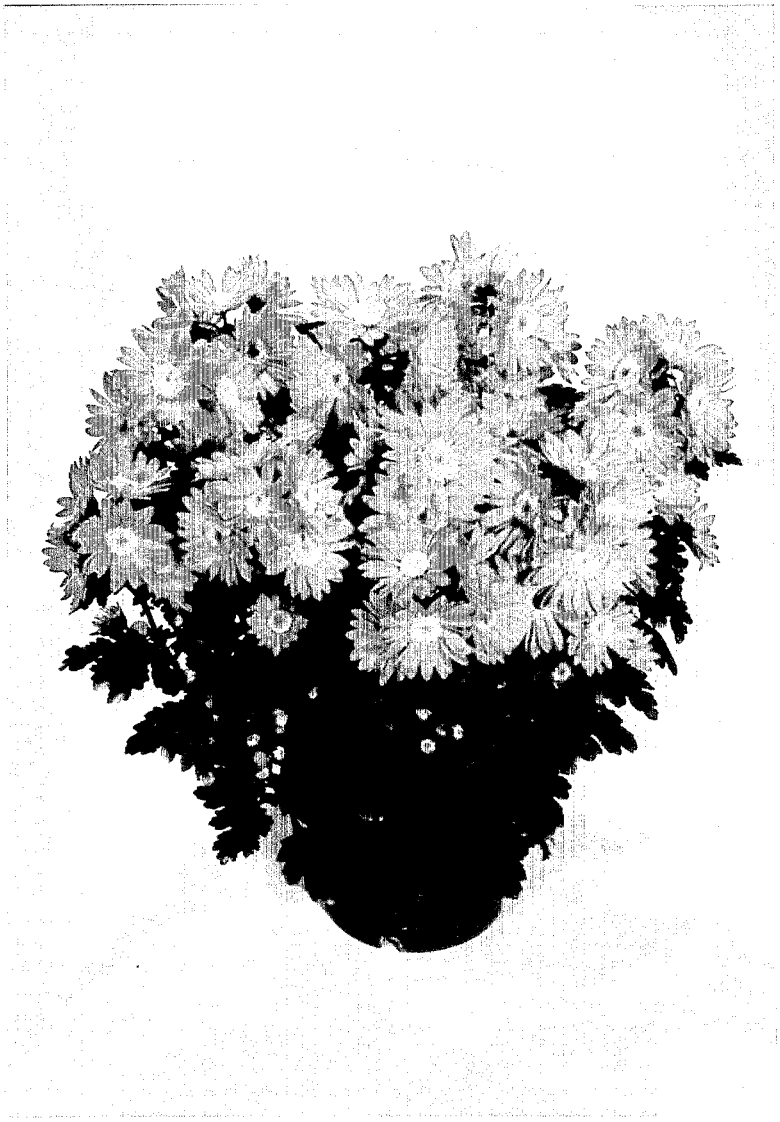

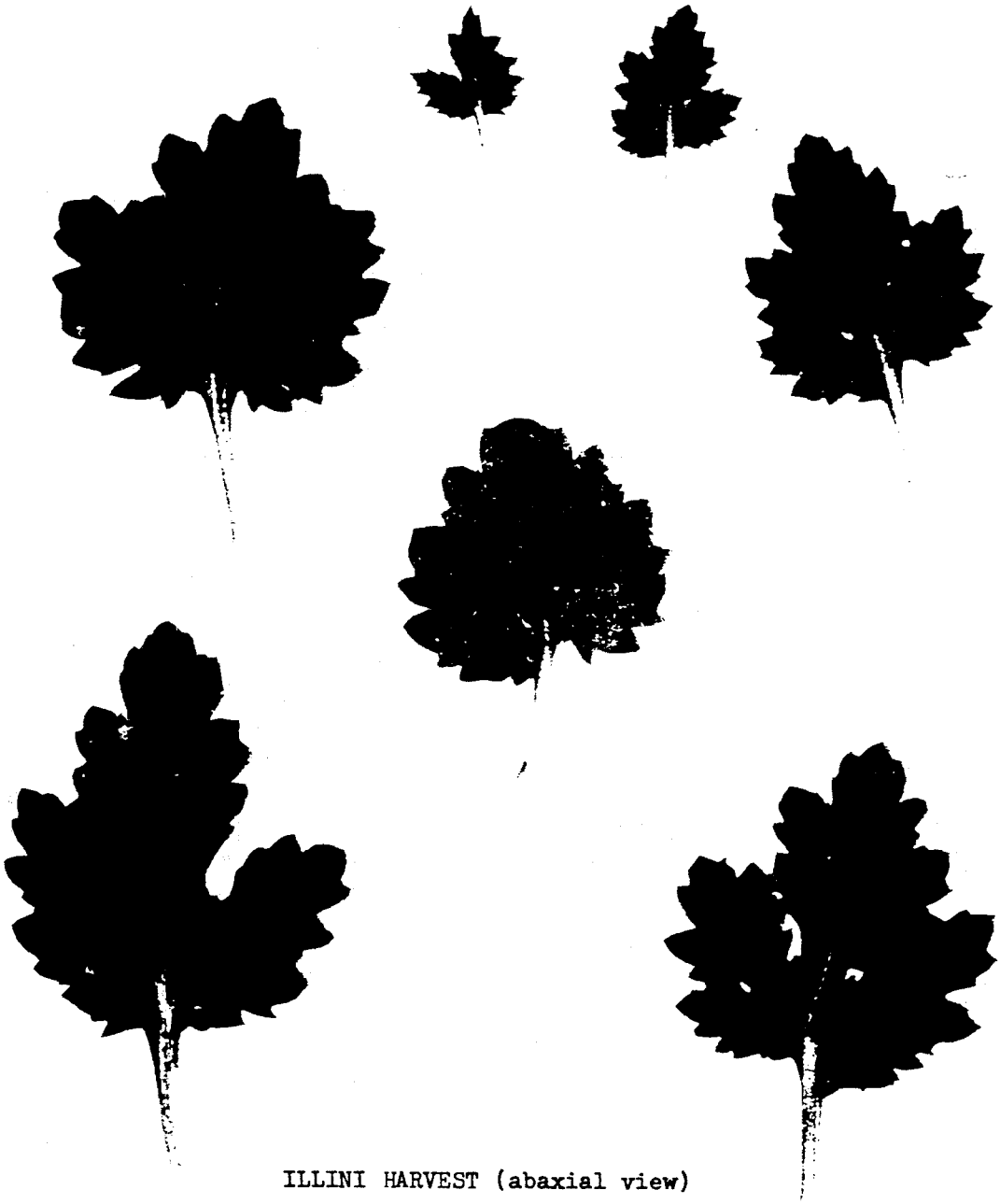
ILLINI HARVEST (abaxial view)